United States Patent [19]

Utterberg et al.

[11] Patent Number: 5,266,072
[45] Date of Patent: * Nov. 30, 1993

[54] GUARDED WINGED NEEDLE ASSEMBLY

[76] Inventors: David S. Utterberg, 1080 Chestnut St., San Francisco, Calif. 94109; Neil J. Sheehan, 2850 Middlefield Rd., Apt. 231, Palo Alto, Calif. 94306

[*] Notice: The portion of the term of this patent subsequent to May 12, 2009 has been disclaimed.

[21] Appl. No.: 948,348

[22] Filed: Sep. 21, 1992

Related U.S. Application Data

[60] Continuation of Ser. No. 761,443, Sep. 18, 1991, abandoned, which is a division of Ser. No. 562,419, Jul. 30, 1990, Pat. No. 5,112,311, which is a continuation of Ser. No. 252,564, Sep. 30, 1988, abandoned.

[51] Int. Cl.$^5$ ............................................. A61M 5/32
[52] U.S. Cl. ................................... 604/177; 604/192; 604/198
[58] Field of Search ............... 604/110, 111, 117, 162, 604/171, 174, 177, 178, 192, 198, 263, 264, 272; 128/919

[56] References Cited

U.S. PATENT DOCUMENTS

| | | | |
|---|---|---|---|
| 3,323,523 | 6/1967 | Scislowicz | 604/162 |
| 3,463,152 | 8/1969 | Sorenson | 604/162 |
| 3,568,673 | 3/1971 | Cowley | 604/162 |
| 3,572,334 | 3/1971 | Petterson | 604/162 |
| 3,595,230 | 7/1971 | Suyeoka . | |
| 3,610,240 | 10/1971 | Harautuein | 604/162 |
| 4,068,659 | 1/1978 | Moorehead | 604/163 |
| 4,329,989 | 5/1982 | Dallons et al. | 604/162 |
| 4,425,120 | 1/1984 | Sampson et al. . | |
| 4,573,976 | 3/1986 | Sampson et al. . | |
| 4,631,057 | 12/1986 | Mitchell . | |
| 4,643,722 | 2/1987 | Smith | 604/192 |
| 4,664,654 | 5/1987 | Strauss . | |
| 4,676,783 | 6/1987 | Jagger et al. . | |
| 4,693,708 | 9/1987 | Wanderer et al. . | |
| 4,731,059 | 3/1988 | Wanderer et al. . | |
| 4,747,836 | 5/1988 | Hughes | 604/192 |
| 4,790,828 | 12/1988 | Drombrowski et al. | 604/198 |
| 4,820,282 | 4/1989 | Hogan | 604/177 |
| 4,840,619 | 1/1989 | Hughes | 604/192 |
| 4,842,587 | 6/1989 | Poncy | 604/198 |
| 4,874,383 | 12/1989 | McNaughton | 604/192 |
| 4,888,001 | 12/1989 | Schoenberg | 604/192 |
| 4,935,012 | 6/1990 | Magre et al. . | |

FOREIGN PATENT DOCUMENTS 729419  3/1966  Canada .................. 604/162

*Primary Examiner*—C. Fred Rosenbaum
*Assistant Examiner*—Mark W. Bockelman
*Attorney, Agent, or Firm*—Gerstman & Ellis, Ltd.

[57] ABSTRACT

A slotted guard for locking a needle in a shielded position as the needle is removed from a patient, and a guarded winged needle assembly including not only such a slotted, locking guard, but also a needle (with a winged hub attached thereto) slidably mounted within the guard. Preferably, the guard's slot has an angled portion so that when the hub and needle are fully retracted within the guard, the needle's tip will be oriented away from the slot. Also preferably, a piece of absorptive material is disposed in the guard to absorb any fluid dripping from the needle tip after the needle has been locked in its retracted position within the guard following an injection. An elongated anchor preferably protrudes outward from the guard so that the needle user may pull the wings of the hub (or a tube attached to the hub) in a conventional manner to retract the needle (and the hub and any tube attached to the needle) away from a patient while the user simultaneously presses the anchor member against the patient to hold the guard fixed. The user will press the anchor member (to hold the guard fixed) until the retracting needle's hub locks into its shielded position within the guard. In this way, the invention eliminates the risk of an accidental needle stick during and after the injection.

7 Claims, 8 Drawing Sheets

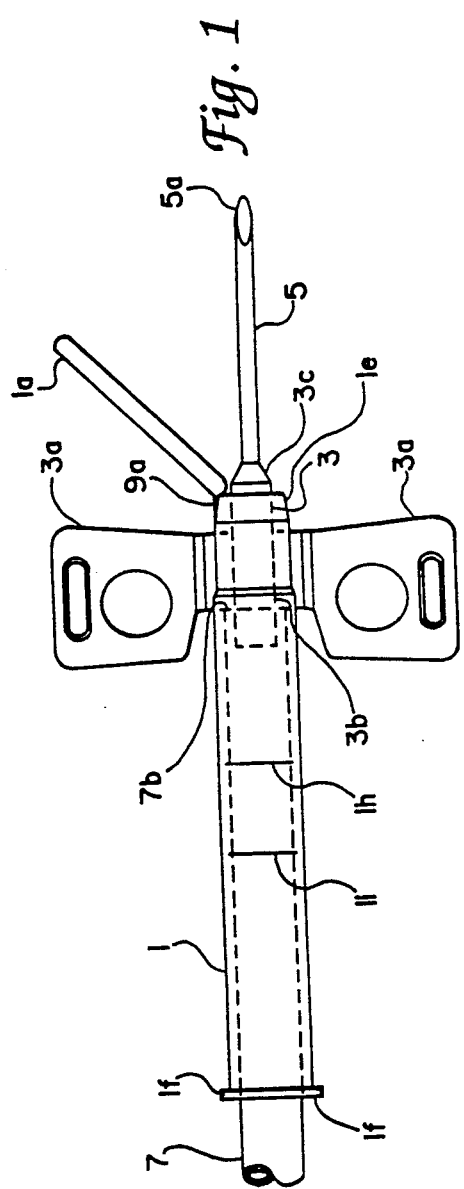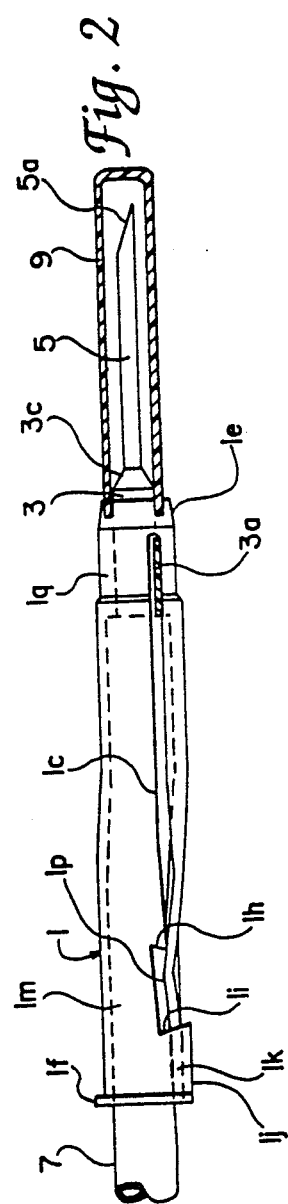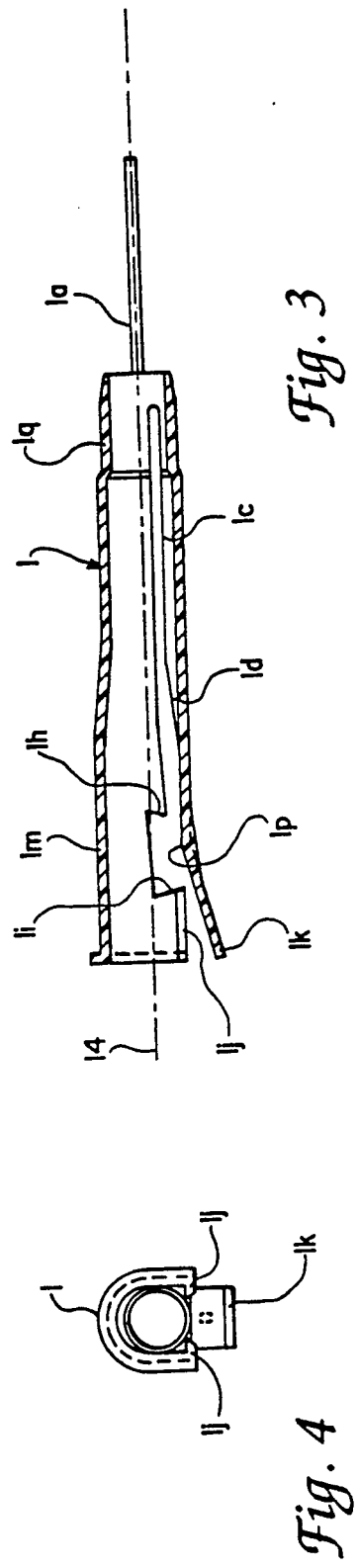

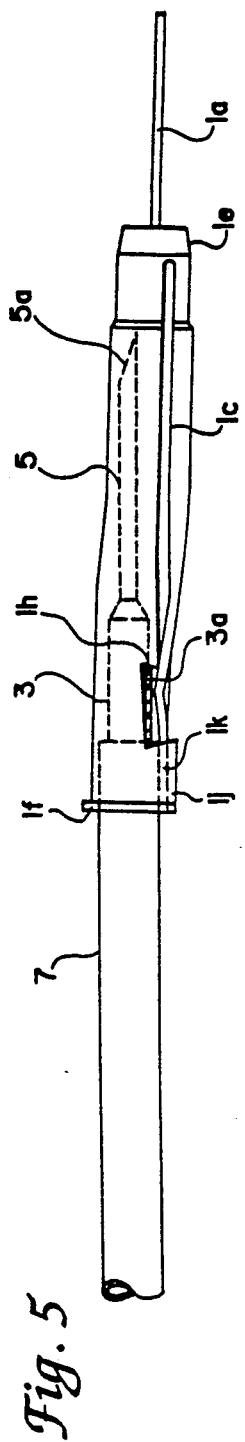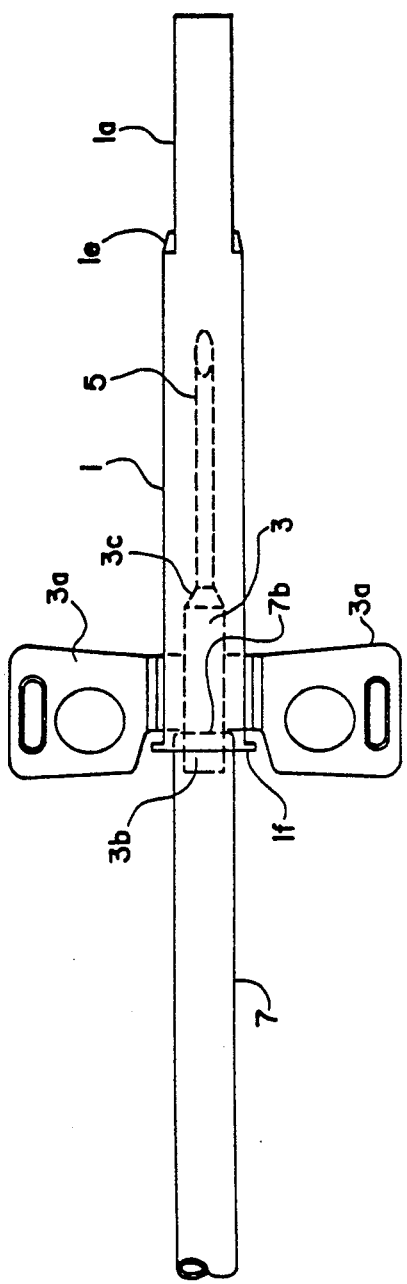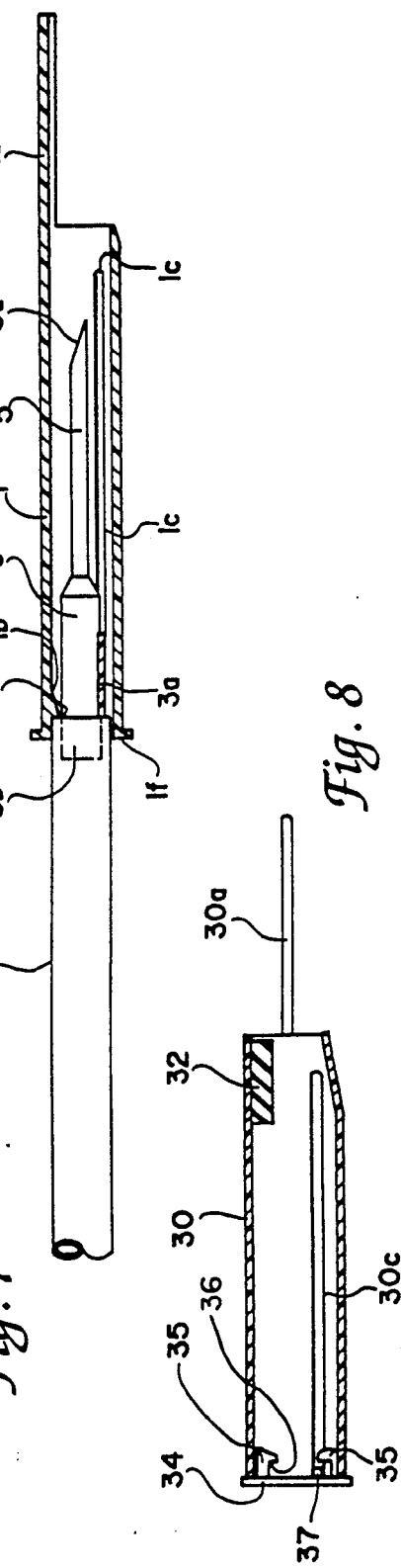

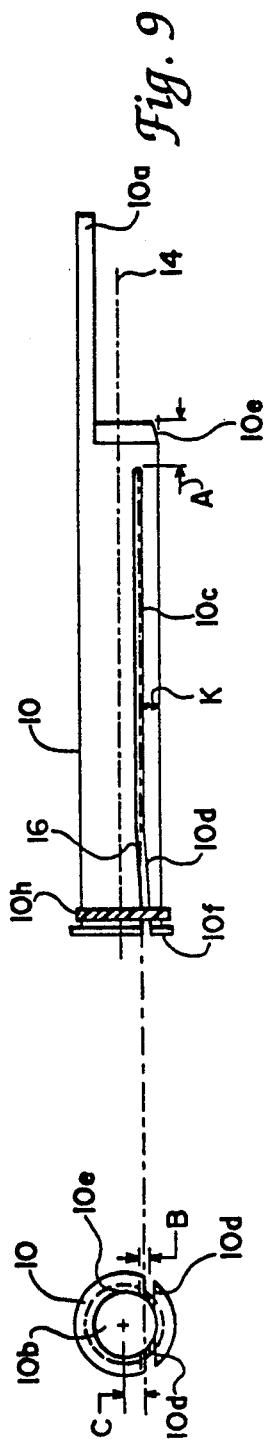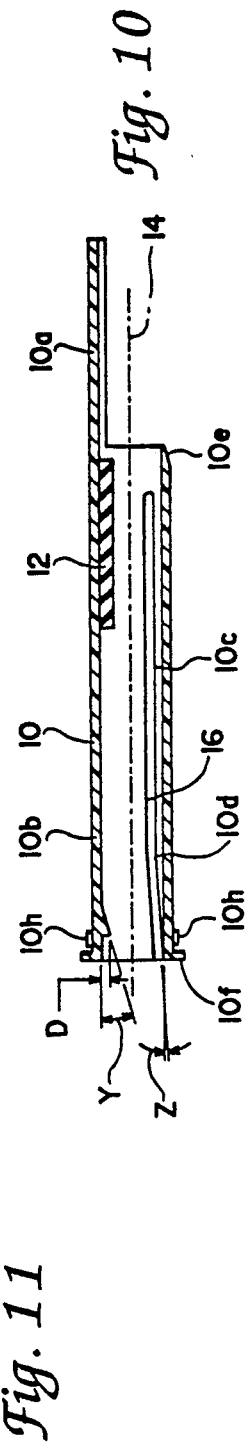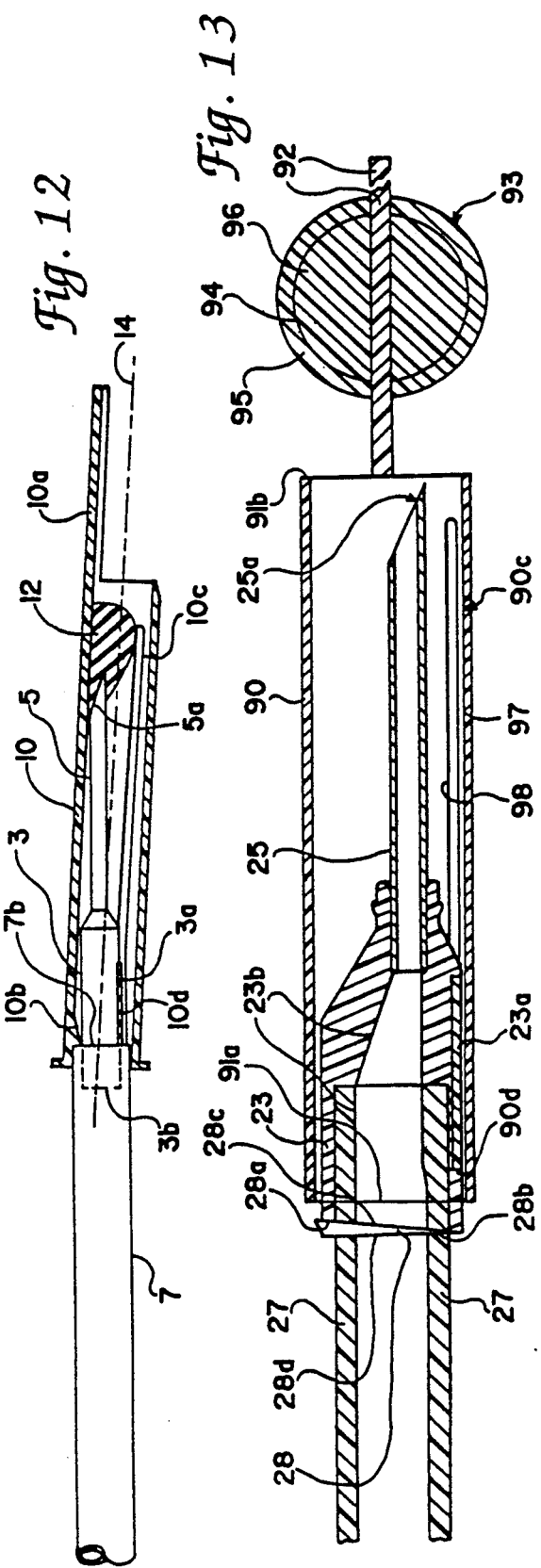

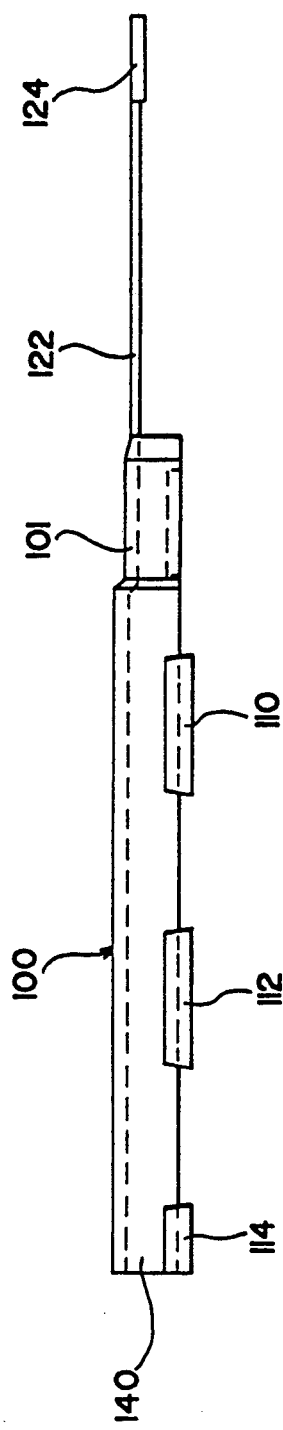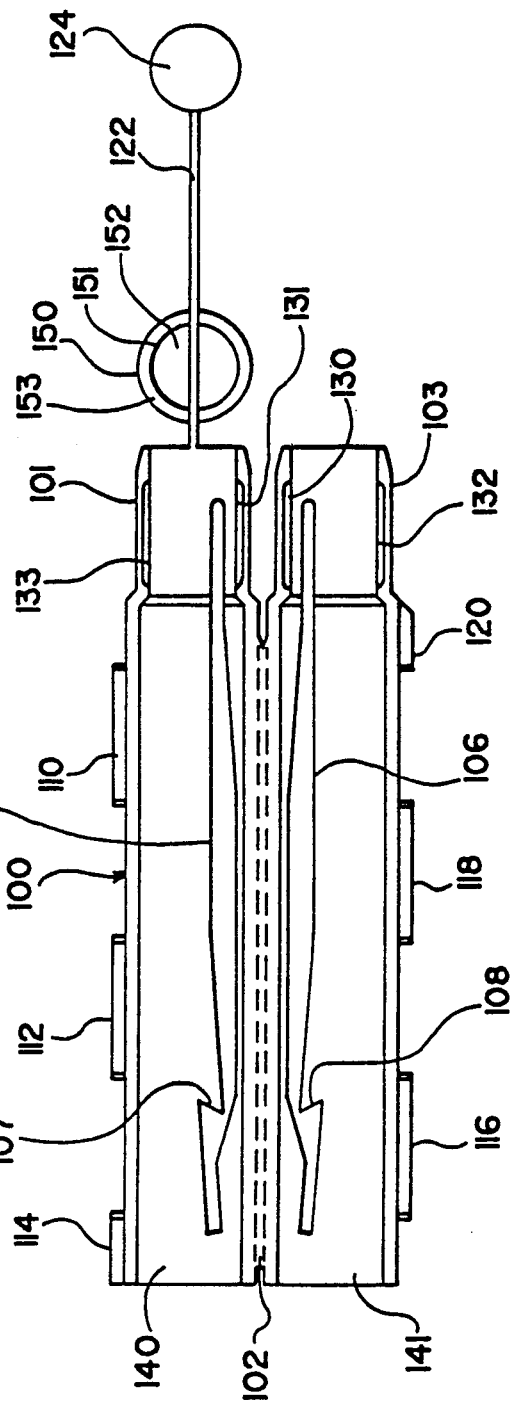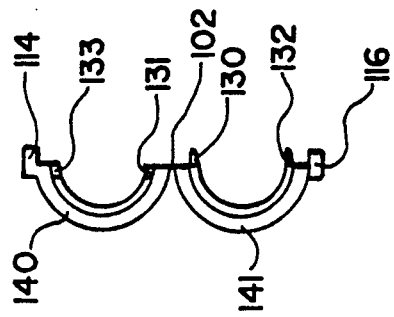

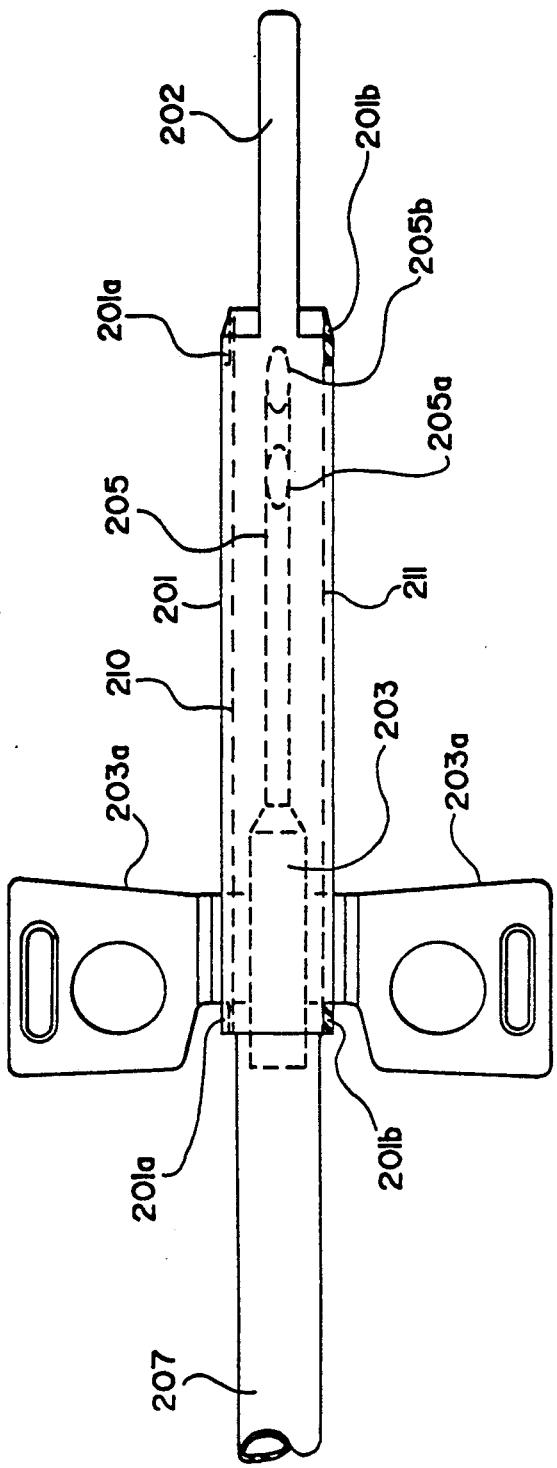

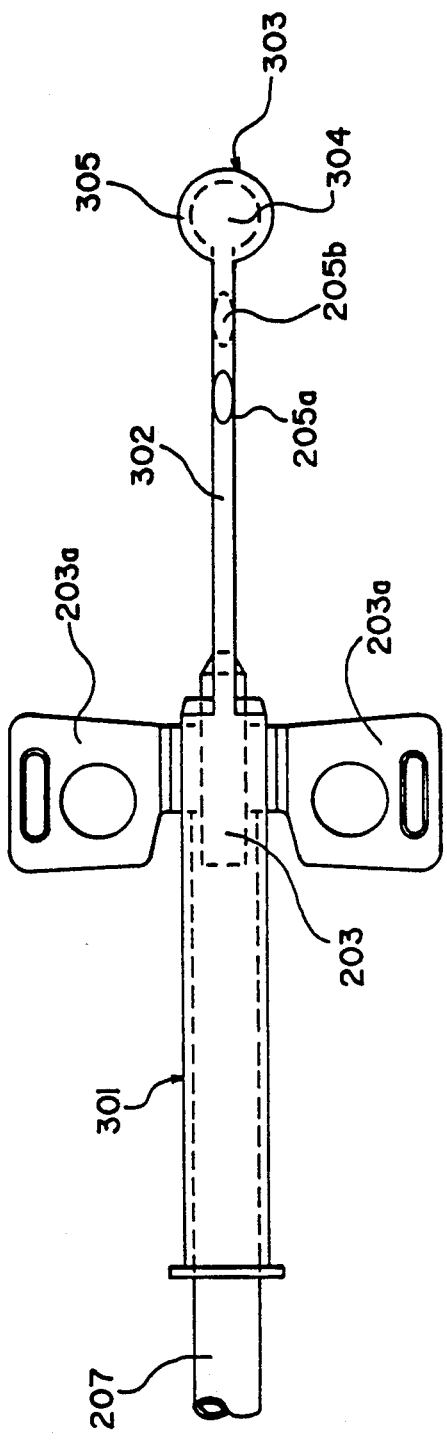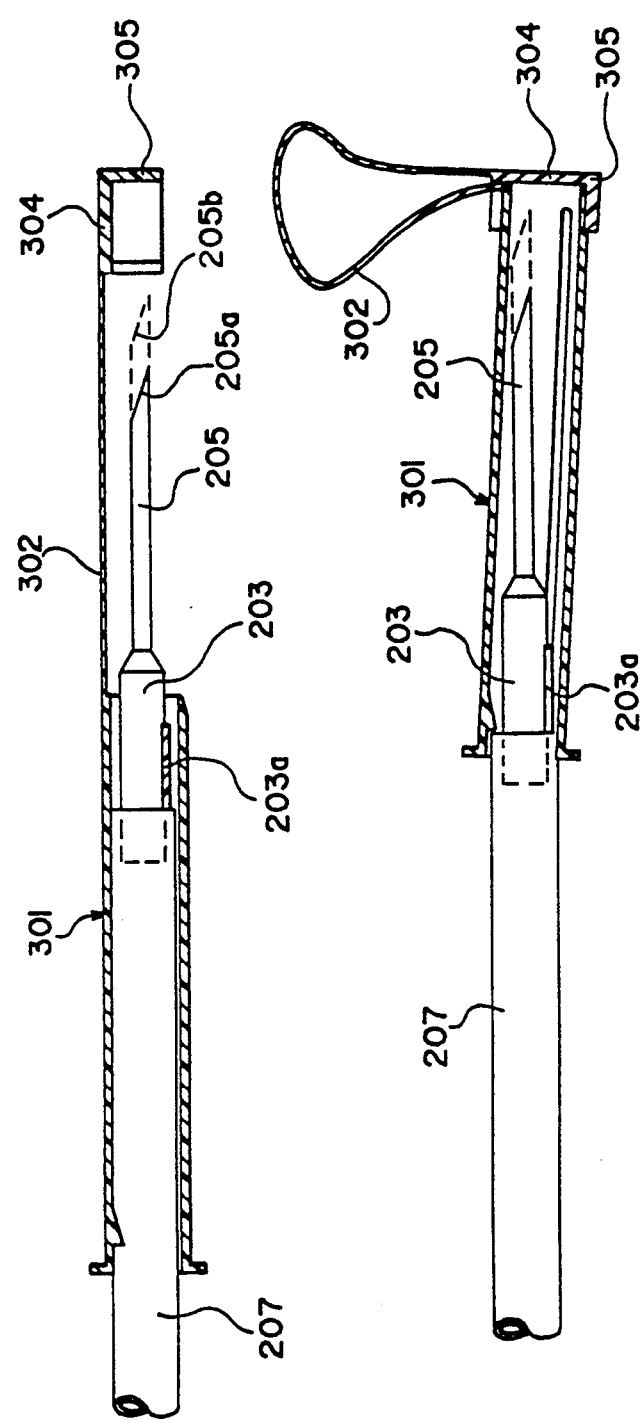

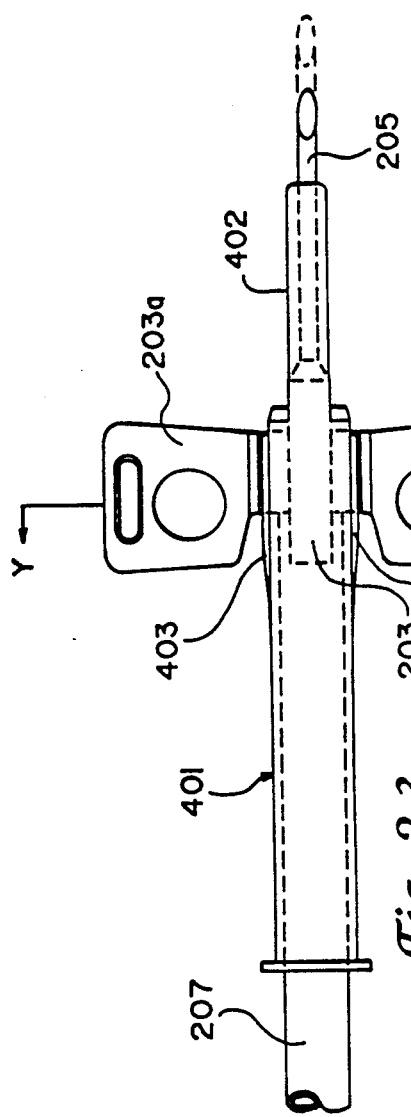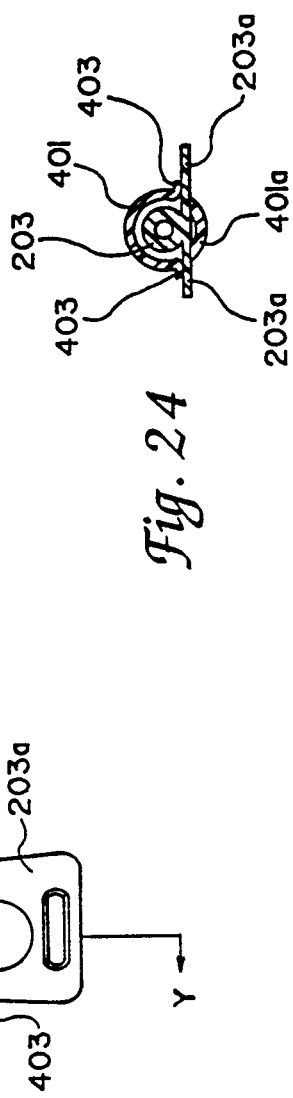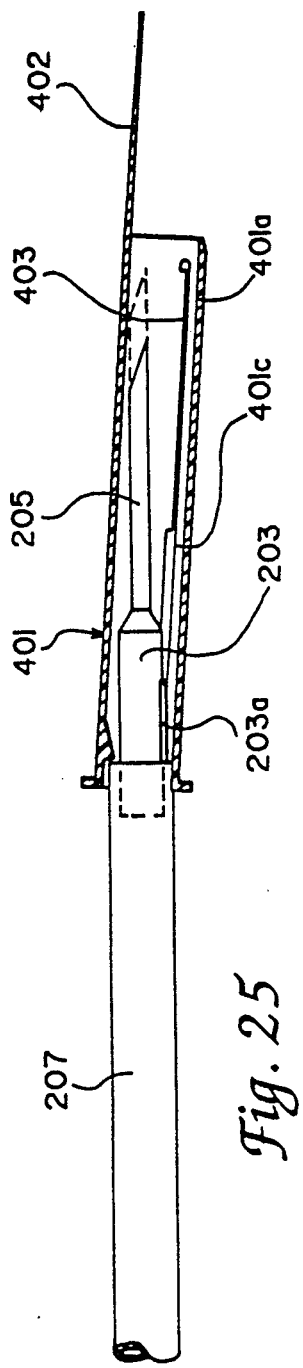

GUARDED WINGED NEEDLE ASSEMBLY

CROSS REFERENCE TO RELATED APPLICATION

This application is a division of U.S. patent application is a continuation of U.S. patent application Ser. No. 761,443, filed Sep. 18, 1991 now abandoned, which, in turn, Ser. No. 562,419 filed on Jul. 30, 1990 now U.S. Pat. No. 5,112,311 which, in turn, is a continuation of U.S. patent application Ser. No. 252,564, filed Sep. 30, 1988, (Abandoned).

FIELD OF THE INVENTION

The invention is a slotted, locking guard for shielding a needle, and a winged needle assembly including a needle, a winged needle hub, and a slotted, locking guard. More particularly, the invention is a slotted guard for locking a needle in a shielded position as the needle is removed from a patient, and a guarded winged needle assembly including such a slotted guard as well as winged needle hub and needle slidably mounted within the guard.

BACKGROUND OF THE INVENTION

Over fifteen million winged infusion, fistula, and pheresis needles are used each month in the United States to deliver sterile fluids to peripheral veins, or to access venous blood supplies for various extracorporeal treatments such as hemodialysis or plasmapheresis. Conventional winged needle assemblies include an elongated hub including flexible wing-like appendages (wings) and a needle attached to a first end of the hub. Conventional needles include "butterfly" needles having gauge in the range 18G-30G for administering medicines of IV fluids, and fistula needles having gauge in the range 12G-17G for moving blood between a patient and an extracorporeal circuit. Tubing is attached to the opposite end of the hub. The tubing may be attached to the inside of the hub (for high flow rate applications), or the tubing may be attached to the outside of the hub (since this type of connection typically is less expensive to achieve).

AIDS is now focusing the medical industry on ways to protect medical workers from infection induced by accidental needle sticks. A National Institute of Health survey in 1987 estimated that more than 800,000 accidental needle sticks occur each year in the United States, almost one accidental stick per nurse per year. Winged needles are just as likely to cause needle stick accidents as are hypodermic and other needles.

"Anti-stick" devices have been proposed, which have sought to sheath or guard a winged needle point after an injection. For example, U.S. Pat. No. 4,676,783, issued Jun. 30, 1987 to Jagger, et al., discloses a retractable winged needle assembly. The needle is mounted on a specially shaped winged inner tube (not a conventional winged needle hub), and the inner tube/needle assembly is slidably mounted within a specially shaped winged outer tube. The inner tube has a first pair of wings, and the outer tube has a second pair of wings. Neither the inner tube nor the outer tube is slotted. The outer tube's wings are gripped to push the needle into the patient's skin, and the inner tube's wings are gripped to retract the needle into the outer tube following an injection.

The apparatus of U.S. Pat. No. 4,676,783 has the disadvantage that both the inner and outer tubes are specially designed. Thus, the apparatus is not usable with a conventional winged needle assembly of the type including a needle mounted on a conventional winged hub. Nor may the winged needle assembly itself be used in a conventional manner. For example, the first pair of wings may not be used to stabilize (by taping) the needle while the needle tip is within a patient.

It has not been known until the present invention how to prevent accidental medical worker sticks due to winged needle injections, while also permitting use of conventional winged needles in a conventional manner.

SUMMARY OF THE INVENTION

In one preferred embodiment, the invention is a slotted guard for locking a needle in a shielded position as the needle is removed from a patient. In another preferred embodiment, the invention is a guarded winged needle assembly including not only such a slotted, locking guard, but also a needle (with a conventional winged hub attached thereto) slidably mounted within the guard. Preferably, the guard's slot has an angled portion (or the hub has an angled locking surface) so that when the sliding hub/needle assembly is fully retracted within the guard, the mechanism for locking the sliding assembly in the retracted position will orient the needle's tip away from the slot. Also preferably, a piece of absorptive material is disposed in the guard, to absorb any fluid dripping from the needle after the needle has been locked in its retracted position within the guard following an injection.

Tubing is preferably attached to the winged hub in a conventional manner. An elongated anchor member preferably protrudes outward from the guard's distal end (substantially parallel to the needle's axis), so that the needle user may pull on the tubing in a conventional manner to retract the needle (with the hub fixedly attached thereto, and the needle fixedly attached to the hub) out from a patient while the user simultaneously presses the anchor member against the patient to hold the guard fixed. The user will press the anchor member (to hold the guard fixed) until the retracting needle is locked in its shielded position within the guard. In this way, the invention eliminates the risk of an accidental needle stick after the needle has penetrated the patient's skin. Preferably, the anchor member is attached to the guard in a manner so that the anchor member does not interfere with the needle while the needle is being introduced into the patient, but so that the anchor member may be conveniently pressed against the patient while the needle is removed from the patient. For example, the anchor member may be an elongated flexible member biased to extend at an acute angle relative to the needle's axis, but capable of being twisted into an orientation substantially parallel to the needle's axis during needle retraction.

The slotted guard may be molded as a single piece having a hinge portion. To install such a one-piece guard around a sliding hub/needle assembly, the guard is folded about its hinge portion and locked (such as by locking tabs) into a generally cylindrical, folded configuration. Alternatively, the guard may be molded in two pieces, which may be heat sealed (or otherwise fastened) together to enclose a sliding hub/needle assembly that has been positioned between the two pieces.

BRIEF DESCRIPTION OF THE DRAWINGS

FIG. 1 is a plan view of a preferred embodiment of the inventive apparatus, including a needle, winged needle hub, and slotted needle guard. The needle is in an extended position relative to the needle guard.

FIG. 2 is a partially elevational, partially cross-sectional side view of the FIG. 1 apparatus, in a plane rotated by 90° with respect to the plane of FIG. 1, and with a protector surrounding the extended needle.

FIG. 3 is a side cross-sectional view of the slotted needle guard of the FIG. 1 apparatus.

FIG. 4 is an end view of the FIG. 3 needle guard.

FIG. 5 is a side elevational view of the FIG. 2 apparatus, with the needle locked in a retracted position relative to the needle guard.

FIG. 6 is a plan view of an alternative embodiment of the inventive apparatus, including a needle, winged needle hub, and slotted needle guard. The needle is in a retracted position relative to the needle guard.

FIG. 7 is a cross-sectional side view of the FIG. 6 apparatus, in a plane rotated by 90° with respect to the plane of FIG. 6.

FIG. 8 is a side cross-sectional view of an another alternative embodiment of the inventive needle guard.

FIG. 9 is a side elevational view of the inventive needle guard in an alternative embodiment of the invention.

FIG. 10 is a side cross-sectional view of the inventive needle guard of FIG. 9.

FIG. 11 is an end view of the FIG. 9 needle guard.

FIG. 12 is a partially side cross-sectional, partially side elevational view of the needle guard of FIG. 10, with a winged hub/needle assembly in a retracted position within the needle guard.

FIG. 13 is a partially side elevational, partially side cross-sectional view of an alternative winged hub/needle assembly of the type useful with the inventive needle guard.

FIG. 15 is a plan view of a preferred slotted needle guard for use with the inventive system, shown in an unassembled, flattened configuration.

FIG. 16 is an end view of the FIG. 15 guard.

FIG. 17 is a side elevational view of the FIG. 15 guard.

FIG. 18 is a plan view of another preferred embodiment of the inventive apparatus, including a slotted, hinged guard, and a sliding needle/hub assembly in a locked, retracted position within the guard.

FIG. 19 is a side cross-sectional view of the FIG. 18 apparatus.

FIG. 20 is a plan view of another preferred embodiment of the inventive apparatus, including a slotted guard with an endcap attached thereto, and a sliding needle/hub assembly in an extended position relative to the guard.

FIG. 21 is a side cross-sectional view of the FIG. 20 apparatus.

FIG. 22 is a side cross-sectional view of the FIG. 20 apparatus, with the sliding needle/hub assembly in a retracted position within the guard and the endcap attached to the guard's right end.

FIG. 23 is a plan view of another preferred embodiment of the inventive apparatus, including a slotted guard, and a sliding needle/hub assembly in an extended position relative to the guard.

FIG. 24 is a cross-sectional view of the FIG. 23 apparatus, taken along line Y—Y of FIG. 23.

FIG. 25 is a side cross-sectional view of the FIG. 23 apparatus, with the sliding needle/hub assembly in a retracted position within the guard.

DETAILED DESCRIPTION OF THE PREFERRED EMBODIMENTS

Figure 14:
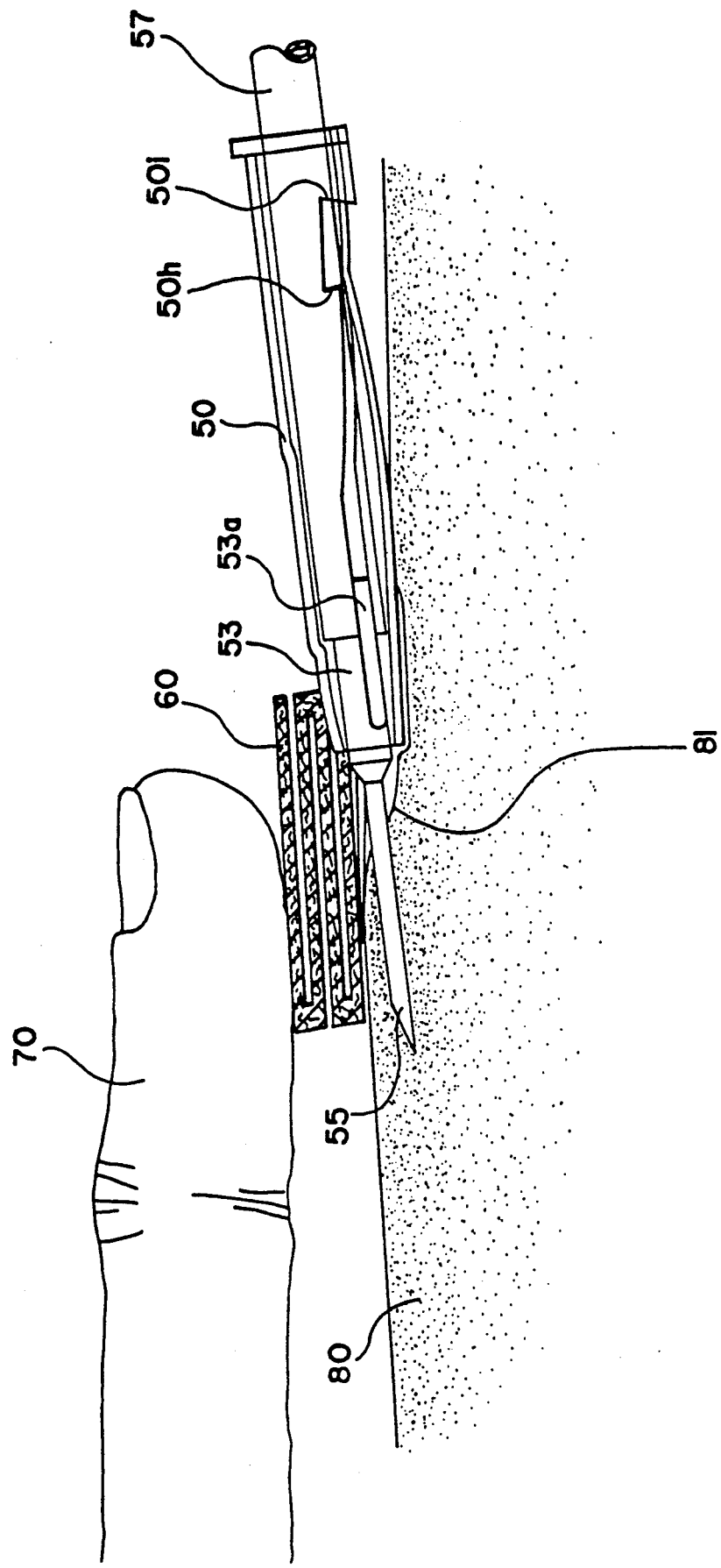
FIG. 14 is a partially side cross-sectional, partially side elevational view of the inventive winged needle guard assembly, with the needle ready to be withdrawn from a patient's skin.

A first embodiment of the invention will be described with reference to FIGS. 1 through 5. In FIG. 1, generally cylindrical, wingless needle guard 1 encloses a central volume containing part of needle hub 3 (shown partially in phantom view) and part of tube 7 (shown partially in phantom view). Tube 7 (also referred to herein as "tubing") is fixedly attached around first end 3b of hub 3. Hollow needle 5 is fixedly attached to second end 3c of hub 3. Hub 3, needle 5, and tube 7 are slidable as a unit relative to guard 1. Needle 5 is in an extended position outside guard 1 in FIG. 1.

Hollow needle 5 is attached to hollow hub 3 in a manner so that fluid may flow between needle 5 and tube 7 through hub 3 (i.e., from within tube 7, through hub 3 and needle 5, and out through tip portion 5a of needle 5, or from within needle 5, through hub 3, and out through tube 7). The invention is particularly useful in the case that needle 5 is an infusion needle.

Hub 3 includes flexible wings 3a, which are typically folded upward (out of the plane of FIG. 1) by the user and gripped in such folded position to insert needle 5 into the skin of a patient. Following insertion of the needle into the patient, wings 3a are typically unfolded and taped to the patient's skin.

Winged hub 3, needle 5, and tube 7 are preferably selected from conventional, commercially available components. Preferably, wings 3a will have thin, flexible portions connecting them to the main, cylindrical body of hub 3, as in many conventional, commercially available winged hub assemblies.

The sidewall of guard 1 is cut away to define a pair of narrow slots 1c (only one of slots 1c is shown in FIGS. 2 and 5). One of wings 3a extends through each slot 1c, so that slots 1c guide wings 3a as the wings are translated axially relative to guard 1. Hub 3, needle 5, and tube 7 are preferably assembled in a conventional manner, and needle 5 is then covered by a conventional sterility protector 9 (shown in FIG. 2). Guard 1 is then attached around the finished needle assembly, so that tip 5a of needle 5 protrudes beyond anchor portion 1a of guard 1. This assembly sequence eliminates the risk that needle 5 or its point 5a will be damaged during assembly.

Although wings 3a and slots 1c are symmetrical in the embodiment of FIGS. 1-5, in other embodiments the wings (and the slots for receiving them) may not all be symmetrically sized and shaped. One slot may be larger (or shaped differently) than the other slot, whether or not the wings are identical. For example, in the hinged guard embodiment (to be discussed in greater detail below with reference to FIGS. 18 and 19), slot 210 between the guard's hinge portions 201a may be shaped differently than slot 211, which is defined by the edges of the guard when such edges meet after portion 201c of the guard is folded relative to portion 201d about hinge portions 201a. Alternatively, one wing (and the corresponding slot) may be omitted entirely from the inventive apparatus.

Protector 9 is installed by pressing it over hub 3, and is retained in place by friction between it and the hub. Protector 9 preserves needle 5's sterility prior to an injection. If protector 9 is installed to cover needle 5 before guard 1 is installed around the needle assembly, protector 9 will also protect needle 5 and point 5a during the process of installing guard 1 around the needle assembly. Protector 9 will be removed (in a conventional manner) by a medical worker just prior to a needle injection. Preferably, there will be little or no friction between protector 9 and guard 1, so that translation of the protector from relative to hub 3 (during removal of the protector) will not cause movement of guard 1. Thus, it is desirable (as shown in FIG. 2) that the left ends of protector 9 will be in contact with hub 3, but guard 1's end portion 1e will have sufficiently large inner diameter so that protector 9 will fit within guard 1 without touching the inner sidewall of end portion 1e. Alternatively, protector 9 may be attached to guard 1 rather than hub 3 and retained in place by friction between it and guard 1.

Protector 9 may also be integrally molded with guard 1, with a break-away portion connecting protector 9 with the rest of guard 1. In this case, guard 1 will maintain its position during removal of protector 9 due to friction exerted by folded wings 3a, which are conventionally gripped in a folded position during this part of the injection procedure.

When the needle is to be removed from the patient, the assembly comprising hub, 3, needle 5, and tube 7 may be pulled toward the left (along the common longitudinal axis of hub, 3, needle 5, tube 7, and guard 1) relative to guard 1 into a retracted, locked position.

In FIGS. 1 and 2, the assembly comprising hub 3, needle 5, and tube 7 (hereinafter denoted the "sliding assembly") is shown in its extended position relative to guard 1, in which needle 5 extends beyond guard 1's end portion 1e, guard 1's anchor portion 1a extends angularly away from needle point 5a, and each of wings 3a abuts the rightmost end of one of slots 1c. The sliding assembly is held in such extended position by friction between guard 1 (which may include an interior retaining notch 1b as shown in FIG. 7, or a tab crest 1p as shown in FIGS. 2 and 3) and tube 7, or friction exerted by the walls of slot 1c on wings 3a. Such friction may be increased by providing a retaining ring or elastic band around the outer surface of guard 1 near flange 1f, or by shaping slots 1c to fit tightly against wings 3a when the sliding assembly is in its extended position.

In FIG. 5, the sliding assembly is shown locked in its retracted position relative to guard 1, in which needle point 5a is retracted within guard 1, each wing 3a is held between shoulders 1h and 1i of one of slots 1c at the slots' left end. To reach the locked position shown in FIG. 5, the sliding assembly comprising hub 3, needle 5, and tube 7 was translated toward the left relative to guard 1 by gripping anchor portion 1a and pulling tube 7 toward the left relative to guard 1, until wings 3a reached shoulders 1i of slots 1c. In the locked position, shoulders 1i prevent further leftward motion of hub 3 relative to guard 1. The sliding subassembly is "irreversibly" slidable in the sense that it may be translated only once from its extended position to its retracted position. Once in its retracted position, it is held therein by action of shoulders 1i and 1h on wings 3a.

The terms "vertical," "upper," "lower," and the like will be used herein to refer to displacements perpendicular to the plane of wings 3a (so that FIG. 1 lies in a vertical plane, and displacement toward the top or bottom of FIG. 2 is vertical displacement). Slots 1c extend axially through a substantial portion of guard 1's sidewall, thus dividing guard 1 into an upper part 1m (the part above slot 1c in FIGS. 2 and 3) and a lower part 1k (the part below slot 1c in FIGS. 2 and 3). Lower part 1k may include a protruding tab crest 1p. One simple technique for forming slots 1c in guard 1 is to mold guard 1 so that slots 1c will extend through an end of guard 1 as shown in FIG. 3. Alternatively, guard 1 may be molded with slots 1c that do not extend through either end of guard 1 (as will be described below in detail, with reference to FIG. 15-19), or guard 1 may be molded without slots and then the slots may be formed by cutting through either one of guard 1's ends. If slots 1c extend through one of guard 1's ends, however, guard 1 may be undesirably flexible due to bending motion of its upper part 1m relative to its lower part 1k. Such undesirable bending motion will alter the width of each slot 1c by varying the distance between guard 1's lower part 1k and end portions 1j of guard 1's upper part 1m. To avoid such undesired bending, guard 1 is preferably shaped so that the upper part end portions 1j form a receptacle into which the left end of lower part 1k may be snapped, so as to interlock the upper part with the lower part 1k as shown in FIG. 2. Alternatively, a compression ring (such as ring 10h to be discussed below with reference to FIGS. 9 and 10, or an elastic band) may be positioned around guard 1 to hold the upper and lower parts of guard 1 together, in order to preserve the desired shape of slots 1c, and to ensure locking retention of the sliding assembly within the guard when the sliding assembly is retracted into the guard.

In each embodiment of the invention, the needle preferably has a low profile relative to the patient's skin when the needle penetrates the skin generally parallel to the skin's surface. The hub wings and the corresponding guard slots (such as wings 3a and slots 1c) may be positioned so that horizontal lines extending through the wings from one slot to the other will be spaced above, below, or coplanar with the horizontal plane through central longitudinal axis 14 of the inventive apparatus. For example, wings 3a and slots 1c of FIGS. 2 and 3 are positioned as closely as practical to the bottom of these Figures (i.e., as closely as possible given other practical constraints on the size and shape of the system components, for example the thickness of guard 1's side walls). Alternatively, wings 3a and slots 1c could be positioned coplanar with central longitudinal axis 14, or above the plane of central longitudinal axis 14.

The vertical thickness of the inner portion of each wing 3a (the portion extending through one of slots 1c) is preferably minimized so that wings 3a may easily be folded vertically by the needle user. It is also desirable that wings 3a have thin inner portions to enable tab crests 1p to bend the wings vertically as the wings slide generally horizontally along slots 1c into engagement with tab crests 1p. Minimizing the vertical thickness of the inner wing portions will allow the corresponding vertical thickness of each slot 1c to be minimized, which will in turn enhance the rigidity of guard 1.

The end portion 1q of guard 1 (in FIGS. 2 and 3) has smaller outer diameter than the rest of guard 1, to facilitate easier bending of the wings 3a when the wings are positioned within the portion of slot 1c at end portion 1q.

To ensure that medical workers have an unobstructed view of the needle's entry into a patient's skin, guard 1's anchor 1a (in the embodiment of FIGS. 1-5) is oriented at an angle away from needle 5's axis. With such orientation, anchor 1a will neither impede needle 5's penetration into a patient's skin nor obstruct the user's view of the needle penetration, and anchor 1a may be pressed flat against the patient's skin as the needle is removed from the patient (in a manner to be described below) to cause the needle to retract into guard 1. Anchor portion 1a may be rod-shaped (with a round or square-shaped profile) or it may be tubular. Preferably, however, it will have a flat profile oriented with flat surfaces in a substantially horizontal plane, as in FIGS. 1, 3, 6, and 7. It is desirable that anchor 1a be flexible and have sufficient length so that it may be positioned flat against a convenient portion of the patient's skin (preferably not precisely over the point of needle entry into the patient) during the needle retraction step.

The angled orientation of anchor 1a in FIGS. 1 and 3 has the additional benefit that anchor 1a will not hinder the operation of rotating a needle mounted within guard 1 (with the needle hub's wings oriented horizontally and extending through slot 1c) by 180° about the guard's axis (clockwise in FIG. 1, from a viewpoint in which needle 5's point 5a points away from the viewer), while the needle remains inserted into the patient. Such 180° needle rotation is often desirable during high fluid intake flow rate operations (particularly during hemodialysis).

In an alternative embodiment (to be described below with reference to FIGS. 6 and 7), anchor 1a has a flat surface oriented in a substantially horizontal plane vertically spaced from the horizontal plane in which needle 5 lies, so that anchor 1a will not impede needle 5's penetration into a patient's skin as the needle approaches the patient between anchor 1a and the patient's skin. In the embodiment of FIGS. 6 and 7, anchor 1a will preferably be sufficiently long so that it will extend beyond the needle point 5a when point 5a has been inserted as far as possible into the patient. In the embodiment shown in FIGS. 6 and 7, anchor portion 1a has a flat surface wider than does anchor 1a in FIGS. 1 and 5.

The operation of removing the needle of the inventive apparatus from a patient will next be described with reference to FIG. 14. To remove the needle (needle 55 in FIG. 14) from the patient, a medical worker would follow the conventional procedure of placing gauze 60 against a first region of the patient's skin 80 at the entry point 81 of the needle, and then pressing the gauze with a finger 70 (and/or thumb) of a first hand against such first region of skin while pulling tube 57 (or wings 53a of winged hub 53) of the sliding assembly within slotted guard 50 of the inventive apparatus with the other hand to remove the needle point from within the patient. To benefit from the invention, the medical worker would press the flexible anchor portion of slotted guard 50 (not shown in FIG. 14) flat against a second region of the patient's skin 80 with a different finger (or thumb) of the first hand while pressing gauze 60 and pulling the tube (or hub wings) toward the right in a conventional manner. The anchor portion (not shown in FIG. 14) is preferably dimensioned and oriented so that it may be pressed against a second region of skin 80 away from the first region. If so, the medical worker may hold guard 50 (including the anchor portion) stationary by pressing the anchor portion against the second skin region with the first hand, while the other hand pulls the sliding assembly toward the right into its retracted position within guard 50 while simultaneously extracting needle 55 from the patient. In this way, the worker is never exposed to the risk of accidentally sticking himself (or herself) with the needle point after the needle point emerges from within the patient.

It is contemplated that, in variations on the embodiment of FIGS. 1–5, anchor 1a may be so short that it does not extend beyond the point 5a of needle 5, or that anchor 1a may be omitted entirely. In either such variation, the medical worker would retract the sliding assembly within guard 1 and simultaneously hold guard 1 stationary by pressing guard 1 (or shortened anchor 1a) against the patient with the same hand (and the same finger or thumb) with which the worker presses the gauze against the patient. In both these variations, the risk is greater that manual pressure on guard 1 or anchor 1a will press gauze 60 against the upper portion of the patient's blood vessel in which needle extends, forcing this upper portion of the blood vessel downward against the retracting needle, potentially causing the retracting needle to scrape (and damage) the blood vessel.

In yet another variation on the embodiment of FIGS. 1–5, anchor 1a is formed of flexible material, and supplied from the manufacturer in a folded orientation in which it is folded (or bent) backward away from needle point 5a so as not to interfere with insertion of the needle into the patient. Anchor 1a may be retained in such folded configuration by any conventional means, such as by removable adhesive tape. In this variation, a medical worker would unfold the anchor prior to removal of the needle from a patient, and would press the anchor against the patient's skin during needle retraction in the manner described above.

In the alternative embodiment of FIGS. 6 and 7, guard 1 includes a different mechanism for locking the subassembly comprising hub 3, needle 5, and tube 7 (the "sliding" assembly) in its retracted position. This locking mechanism includes a retaining notch 1b which extends radially inward from the sidewall of guard 1 near flange 1f. Notch 1b will exert leftward force on end surface 7b of tube 7, thus preventing the sliding assembly from returning to its extended position and retaining the sliding assembly in its retracted position. In the embodiment of FIGS. 6 and 7, slots 1c in guard 1's side wall are straight; not angled at the left end as in the embodiment of FIGS. 1–5 and 9–12.

In any of the inventive embodiments, tube 7 may be formed conventionally from flexible plastic (such as polyvinyl chloride plastic), so that flexible tube 7 may deform temporarily (i.e., become temporarily indented by action of a rigid notch, such as rigid notch 1b, against tube 7) in order to clear the rigid notch during a transition from the sliding assembly's extended configuration to its retracted configuration.

Guard 30 of FIG. 8 is a cross-sectional side view of an alternative embodiment of the needle guard of the invention. Guard 30 includes flat anchor portion 30a (having flat, horizontally oriented surfaces), and pair of slots 30c in its side wall (only one of slots 30c is visible in FIG. 8). Each slot 30c is substantially straight (as are slots 1c in the embodiment of FIGS. 6–7), in contrast with slots 1c of FIGS. 2 and 3, and slots 10c of FIGS. 9–12 (to be described below). Sponge 32, shown mounted within guard 30 in a dry, compressed state, is provided for receiving fluid that may drip from a needle after the needle is withdrawn within guard 30 after an injection. By absorbing such dripping fluid, sponge 32 reduces the chance that needle users may be infected by the fluid. Ring 34, which includes notches 35 and aligning tabs 37, is fixedly attached to the end of guard 30 opposite anchor 30a. Each notch 35 includes a snap ridge 36 for engaging the end surface 7b of a tube (such as tube 7 of FIGS. 6–7), in the same manner as does notch 1b in FIG. 7, to lock a hub/needle subassembly within guard 30 into its retracted position. Each aligning tab 37 is oriented and dimensioned to slide within one of slots 30c, so as to properly align ring 34 relative to guard 30 during the operation of attaching ring 34 to guard 30.

FIGS. 9, 10, 11, and 12 show another alternative embodiment of the inventive winged needle guard, including an angled (or curved) slot in its sidewall, rather than a straight slot, and including sponge 12. Guard 10's slot includes a first portion 10c oriented substantially parallel to longitudinal axis 14 of guard 10, and a second portion 10d oriented at an acute angle Z (shown in FIG. 10) relative to axis 14. Angle Z is preferably within the ranges of from about 3° to 4° in the embodiment shown in FIGS. 9 and 10. Although sharp corner 16 defines the intersection of portions 10c and 10d in FIGS. 9 and 10, in an alternative embodiment the intersection may instead by defined by a curved slot portion. FIG. 11, an end view of FIG. 9, shows that two slot portions 10d are symmetrically positioned on opposite sides of guard 10, for receiving a pair of oppositely oriented hub wings prior to attachment of compression ring 10h around guard 10.

The purpose for including angled slot portion 10d may be understood with reference to FIG. 12. FIG. 12 shows guard 10 of FIGS. 9–11, with a sliding assembly (comprising hub 3, hub wings 3a, needle 5, and tube 7) in a retracted position within needle guard 10. Each wing 3a of hub 3 extends through one of slot portions 10d in the FIG. 12 configuration, thus orienting needle 5's longitudinal axis at an angle relative to longitudinal axis 14 of guard 10 so that needle point 5a abuts guard 10's sidewall. This retracted needle orientation is desirable in order to maximize the distance between slot 10c and point 5a, and thus reduce the risk that point 5a will protrude out from slot 10c during handling of guard 10 following an injection. In the FIG. 12 embodiment, the sliding assembly is held in its retracted position by the leftward force exerted by notch 10b on end surface 7b of tube 7. In FIG. 12, slot 10c is positioned below the guard's central axis so that needle point 5a abuts the guard's upper sidewall. Alternatively, if slot 10c were positioned above the guard's central axis, the slot would be angled to cause needle point 5a to abut the guard's lower sidewall (to maximize the distance between the guard and the needle point).

Sponge 12 is mounted within guard 10 to soak up fluids that may drip from needle 5 after an injection, thus reducing the risk that such fluids (such as blood) will drip out of guard 10 and cause infection. Sponge 12 is shown in its dry compressed state in FIG. 10. The small volume of sponge 12 in its dry, compressed state provides clearance within guard 10 for mounting a sliding needle/hub assembly (in the sliding assembly's extended position). FIG. 12 shows sponge 12 in its wet, expanded state. In FIG. 12, a needle/hub subassembly has been retracted within guard 10 after an injection, and sponge 12 has expanded due to absorption of fluid dripping from the needle. It should be appreciated that the term "sponge" is used herein to denote a piece of any type of highly absorbent material, including natural sponge material, synthetic sponge material, and other absorbent material.

Flange 10f, fixedly attached outside guard 10 (or integrally molded with guard 10), serves to retain elastic compression ring 10h in place for preventing the upper and lower parts of guard 10 from separating radially. Compression ring 10h may be a rubber band, or another type of elastic band. Alternatively, compression ring 10h may be replaced by a C-shaped or O-shaped rigid ring closure (which may be metal) fixedly attached (such as by a heat seal) to guard 10.

Preferably for use with fistula needles, guard 10 is formed of thin polypropylene plastic (i.e., with inner diameter on the order of 5.5 mm, and sidewall thickness on the order of 0.75 mm), and has overall length on the order of 64 mm (from flange 10f to the tip of anchor 10a). Anchor 10a preferably has length on the order of 19 millimeters from edge 10e of guard 10 to anchor 10a's tip. Flange 10f preferably has thickness of about 0.75 mm. For use with a needle having length in the range of about 1 inch to about 1.25 inches, the distance A between beveled edge 10e and the right end of slot 10c is preferably about 3 mm, and the angle Y between retaining notch 10b and axis 14 is preferably 15°. The distance D between guard 10's sidewall and the tip of notch 10b is preferably on the order of 0.75 mm. For use with smaller needles (such as infusion needles), the preferred dimensions will be scaled down.

In general, needle 5 should be mounted so as to have a low profile relative to the patient's skin when needle 5 penetrates the skin generally parallel to the skin's surface. Such low needle profile is desirable because the narrow inner diameter of typical needles used with the invention provides great resistance to fluid flow. Thus, in typical winged needle assemblies, the needle length should be a short as possible (while still long enough to reach a deep vein). Raising the needle profile necessitates use of a longer needle, thus worsening the described flow resistance problems.

The angle of edge 10e of guard 10 helps reduce wasted needle length.

The length A, between the right end of slot portion 10c and the right end of edge 10e, will ideally be sufficiently long that needle point 5a will rest between the right end of slot portion 10c and the right end of edge 10e when locked in its retracted position. If point 5a is too close to edge 10e, it could accidentally prick an errant finger. If point 5a is adjacent slot portion 10c when locked in its retracted position (as shown in FIG. 12) there is a slight chance that bending of guard 10 might allow point 5a to protrude out through slot portion 10c. It is desirable that such distance A be sufficiently short to avoid unnecessarily limiting the length of needle available for insertion into the patient's skin.

For use with typical wings 3a, the wing slot (including portions 10c and 10d) will typically have thickness B substantially equal to 0.75 mm, and the distance C between axis 14 and the upper edge of slot portion 10d at rim 10f will typically be substantially equal to 1.7 mm (where the outer diameter of guard 10 is 7 mm).

It is specifically contemplated that the dimensions of any of the preferred embodiments described herein may be scaled up or down to accommodate any needle, for example, any needle having gauge in the range from 12G through 30G.

FIG. 13 shows an alternative winged hub/needle subassembly in a retracted position within slotted needle guard 90. The winged hub/needle subassembly of FIG. 13 includes needle 25, hub 23, and tube 27. Hub 23 includes wings 23a. Needle 25 is fixedly attached to hub 23 in the same manner as needle 5 is attached to hub 3 of FIGS. 1–5 (and hub 3 of the FIG. 6–7 embodiment). Unlike in the FIG. 1–5 and FIG. 6–7 embodiment, however, tube 27 is attached to the radially inner surface 23b of hub 23, rather than to the radially outer surface of the hub. The hub/needle subassembly of FIG. 13 is preferable to that of FIGS. 1-7 for applications in which high fluid flow rates between the tip of the needle (5 or 25) and the tube (7 or 27) are desired. Needle guard 90, which has an inner diameter slightly greater than the outer diameter of hub 23, is mounted around hub 23 and needle 25.

Because hub 23 is mounted around tube 27, there is no shoulder or edge of tube 27 corresponding to surface 7b of tube 7. Instead, a ring-shaped member, such as ring 28, is fixedly mounted around tube 27 to engage with a locking notch, such as notch 1b of FIG. 7 (or notch 35 of FIG. 8). Thus, when tube 27 and winged hub 23 are mounted within a slotted guard having a locking notch (as when tube 27 and hub 23 are substituted for tube 7 and hub 3 in FIG. 7), the locking notch (i.e., notch 1b of FIG. 7), will restrain motion of needle 25 and hub 23 toward the right (to retain needle 25 and hub 23 in a retracted, locked position within the guard) by engaging ring 28. Ring 28 may be integrally molded with hub 23, or it may be glued or otherwise fixedly attached to hub 23.

Ring 28 in FIG. 13 has non-uniform thickness, with a relatively thicker upper portion 28a and a relatively thinner lower portion 28b. The front surface 28c of ring 28 is oriented at an acute angle with respect to ring 28's substantially vertical back surface 28d. Thus, when thicker upper portion 28a is engaged with a locking notch (such as locking notch 1b of FIG. 7), the force exerted by the notch on ring 28 will rotate the FIG. 13 sliding assembly counter-clockwise, so that needle point 25a of retracted needle 25 will point upward, toward the upper sidewall of the guard surrounding retracted needle 25. By including such a non-uniform ring 28, use of an angled slot becomes unnecessary to ensure that needle point 25a will be positioned away from such slot when the FIG. 13 sliding assembly is locked in its retracted position. Accordingly, a slotted guard having a non-angled slot (such as guard 30 of FIG. 8, or guard 90 having non-angled slot 90c, as shown in FIG. 13), may be used with the hub/needle assembly of FIG. 13.

Rather than a locking notch (such as notch 1b) positioned away from the guard slot, the slotted guard used to enclose the FIG. 13 assembly may include a notched slot locking mechanism (such as slot 1c of FIGS. 1-5, with shoulders, or "notches," 1h and 1i) to lock the FIG. 13 assembly in its retracted position within the guard.

Alternatively, the guard and slot may be "notchless", as are guard 90 and slot 90c of FIG. 13. Guard 90 and ring 28 are dimensioned so that the sliding hub/needle assembly may be locked in a retracted position within guard 90 in the following manner. When the hub/needle assembly is in its extended position, ring 28 will be enclosed within guard 90 (with ring 28 and the portion of tubing 27 adjacent ring 28 slightly compressed or twisted by the radially inward force exerted thereon by guard 90. The hub/needle assembly is then pulled to the left until ring 28 translates past left end portion 91a of guard 90 and emerges from within guard 90. At this point, ring 28 and the adjacent portion of tubing 27 will relax from their compressed configuration (i.e., they will expand or become untwisted) so that "relaxed" ring 28 will be prevented from reentering guard 90 by action of end portion 91a against ring 28. The hub/needle assembly will remain locked in this "retracted" position (with ring 28 outside, but within a short distance, of guard 90) due to the force exerted on wing 23a of hub 23 by the left end 90d of guard 90.

Endcap 93 of FIG. 13 is another optional feature of the invention, which may be attached to (or integrally molded with) the anchor of any of the inventive embodiments. In FIG. 13, flexible anchor 92 is attached to guard 90, and endcap 93 is attached to anchor 92. Endcap 93 comprises a disk (having outer portion 95 and inner portion 96), and a ridge 94 separating portions 95 and 96. After the sliding hub/needle assembly is locked in its retracted position within guard 90 as shown in FIG. 13, flexible anchor 92 may be flexed out of the plane of FIG. 13 to position the endcap adjacent right end portion 91b of guard 90, so that ridge 94 may be snapped together with end portion 91b (so that ridge 94 fits tightly inside of the inner surface of guard 90's sidewall). By so connecting endcap 93 with guard 90, a fluid seal is formed preventing any fluid that may drip from needle 25 from flowing out through the right end portion 91b of guard 90.

A preferred embodiment of the inventive slotted needle guard (identified by reference numeral 100) will next be described with reference to FIGS. 15-17. Guard 100 includes hinge portion 102 (connecting two generally half-cylindrical portions 140 and 141). Locking tabs 110, 112, and 114 protrude from an edge of portion 140. Locking tabs 116, 118, and 120 protrude from an edge of portion 141. An anchor, comprising anchor stem 122, flat anchor plate 124, and flat endcap 150, is attached to end portion 101 of guard 100. Endcap 150 includes inner and outer disk portions 152 and 153, and circular ridge 151 separating portions 152 and 153. Hub wing slots 105 and 106, having notched portions 107 and 108 respectively, extend through guard 100. Slots 105 and 106 are formed during the process of molding flat, unassembled guard 100.

Guard 100 is molded in a generally flat, open configuration as shown in FIGS. 15-17. In order to install guard 100 around a winged hub/needle assembly (of any of the types described above), the hub wings protruding out from such assembly are extended through slots 105 and 106, and portions 140 and 141 of guard 100 are then folded together about hinge portion 102 to enclose the hub/needle assembly, and so that tab 116 locks between tabs 112 and 114, tab 118 locks between tabs 110 and 112, and tab 110 locks between tabs 118 and 120. Tabs 110, 112, 114, 116, 118, and 120 thus lock together to retain guard 100 in its assembled configuration.

When locked in its assembled configuration, guard 100 has a generally cylindrical shape, with its longitudinal cylinder axis parallel to anchor stem 122. If the plane of anchor plate 124 is defined as the horizontal plane, then when guard 100 has been folded and locked in its cylindrical, assembled configuration, the plane intersecting hinge 102 and locked tabs 110, 112, 114, 116, 118, and 120 is oriented substantially vertically, and hinge 102 extends horizontally along the bottom of assembled guard 100.

Tabs 130 and 132 extend (vertically out of the plane of FIG. 15) from guard 100's end portion 103, and slots 131 and 133 extend through guard 100's end portion 101. Tabs 130 and 132 are sized and positioned to fit tightly within slots 131 and 133, respectively, when guard 100 is folded into its cylindrical assembled configuration. Friction between tabs 130 and 132 and the walls of slots 131 and 133 helps to maintain guard in its cylindrical assembled configuration.

The flat surface of anchor plate 124 may be pressed against a patient's skin during the operation of needle withdrawal from the patient, to allow the needle to translate into a locked, retracted position within assembled guard 100. Anchor stem 122 is desirably flexible to permit convenient positioning of plate 124 and to permit endcap 150 to be snapped together with guard 100's right end (with ridge 151 locked inside the inner cylindrical surface of guard 100's sidewall).

FIGS. 18 and 19 show yet another preferred embodiment of the inventive apparatus. Hub 203 has two wings 203a, one extending through slot 210 in the sidewall of guard 201 and the other extending through slot 211 in the sidewall of guard 201. Tubing 207 is attached around one end of hub 203, and needle 205 is attached to the other end of hub 203. The entire assembly comprising hub 203, needle 205, and tubing 207 is slidably mounted within guard 201. If tubing 207 or wings 203a are pulled toward the left from an extended position (with needle 205's point outside guard 201), hub 203 and needle 205 will translate toward the left as they retract into guard 201. When hub 203 occupies the position shown in FIGS. 18 and 19, the rightmost end surface 207a of tubing 207 abuts locking notch 209, so that the leftward force exerted by notch 209 on tubing 207 (and the rightward force exerted by the left edge of each slot on the wing 203a extending therethrough) will lock the sliding hub/needle assembly in its fully retracted position.

Guard 201 is preferably dimensioned as shown, to accommodate a variety of the most commonly used conventional needles. Thus, where needle 205 is a conventional needle having a length of one inch, needle 205's point will occupy position 205a, and where needle 205 is a conventional needle having a length of one and one quarter inches, needle 205's point will occupy position 205b. Both needle point positions 205a and 205b are safely within guard 201 when the needle is locked in its retracted position.

Anchor portion 202 of guard 201 has a flat surface lying in the plane of FIG. 18.

Guard 201 is preferably molded in a generally flat, one-piece, unassembled configuration. Guard 201 attains its generally cylindrical shape (shown in FIGS. 18 and 19) only after generally half-cylindrical portions 201c and 201d of guard 201 are folded together about side hinge portions 201a and the edges of portions 201c and 201d are sealed together at sealing regions 201b.

To install guard 201 around the sliding hub/needle assembly, the upper one of hub wings 203a is extended through slot 210 between side hinge portions 201a, and first portion 201c of guard 201 is then folded about hinge portions 201a relative to second portion 201d of 201, so that the edges of portions 201c and 201d meet at side sealing regions 201b. As the edges of portions 201c and 201d meet, they define second slot 211. Slot 211 is thus formed around the lower one of wings 203a during the operation of folding portion 201c about hinge portions 201a, so that such lower wing extends through the newly formed slot 211. The edges of portions 201c and 210d may be shaped so as to define a slot 211 identical to slot 210. Alternatively, the edges of portions 201c and 201d may be shaped so as to define a slot 211 shaped differently from slot 210 (for example, the central portion of slot 211 may be narrower than that of slot 210, where slot 210 has a wide central portion to facilitate easier insertion of the upper wing 203a through slot 210).

At each region 201b, portion 201c is fixedly attached by a heat seal (or an adhesive layer, or snaps) to portion 201d in order to maintain guard 201 in the cylindrical assembled configuration shown in FIGS. 18 and 19. Alternatively, one or more locking tabs may protrude from the edges of either or both of portions 201c and 201d, to enable portions 201c and 201d to be snapped together (and remain snapped together by friction) at regions 201b. Portions 201c and 201d need not include locking tabs, but may be otherwise shaped so that they will snap together (and remain held together by friction) at regions 201b.

In a variation on the FIG. 18–19 embodiment, hinge portions 201a are omitted from guard 201, so that guard 201 consists of two separate, generally half-cylindrical portions 201c and 201d. To install such a two-piece guard 201 around a sliding hub/needle assembly (in this variation on the FIG. 18–19 embodiment), the half-cylindrical portions are connected together (by a heat seal, by an adhesive layer, or by snapping together) at all four of regions 201a and 201b.

In the assembled one-piece guard of FIGS. 18 and 19, slot 210 is formed as an orifice through the hinge region of one-piece guard 201 between hinge portions 201a during the molding process (in the same manner as slots 105 and 106 are formed in one-piece guard 100 shown in FIG. 15). Slot 211 (which is not shown in FIG. 19, but which is positioned symmetrically on the side of guard 201 opposite slot 210 as shown in FIG. 18) is a gap between the connected edges of portions 201c and 201d which is bounded at the ends by regions 201b. In contrast, both slots of the two-piece guard described in the preceding paragraph are defined by the connected edge portions of the guard's half-cylindrical component members between sealing regions 201a and 201b (in other words, one slot is a gap between the connected edges between regions 201a, and the other slot is a gap between the connected edges between regions 201b). Thus, in this latter two-piece guard embodiment, no slot orifice need be formed through either half-cylindrical guard portion during the operation of molding the half-cylindrical guard portions.

FIGS. 20–22 show another preferred embodiment of the invention. In FIGS. 20–22 the FIG. 18 sliding assembly (comprising winged hub 203, needle 205, and tubing 207) is mounted within slotted guard 301. Flexible anchor stem 302 connects endcap 303 with guard 301. Endcap 303 is employed as an anchor in the same manner as anchor 124 of FIG. 15. Member 303 also functions as an endcap, which may be snapped onto guard 301's right end as shown in FIG. 22.

Endcap 303 includes disk portion 304 and generally cylindrical wall portion 305. When anchor stem 302 is flexed as shown in FIG. 22, wall portion 305 may be snapped over the outside of guard 301's sidewall so that endcap 303 prevents fluid flow from needle 205 out through the right end of guard 301.

FIGS. 23–25 show another preferred embodiment of the invention. In FIGS. 23–25, the FIG. 18 sliding assembly (comprising winged hub 203, needle 205, and tubing 207) is mounted within slotted guard 401. Anchor portion 402 of guard 401 is oriented in the plane of hub 203's wings 203a. A pair of slots 401c extend through the sidewall of guard 401 to receive wings 203a. In order to reduce the flow of fluid from guard 401's interior to the surrounding environment (after needle 205 has been retracted within guard 401 after an injection), guard 401's sidewall is molded to have curtain portions 403. Curtain portions 403 normally fit tightly against lower sidewall 401a of guard 401 (which defines the lower edge of slots 401c), as shown in FIG. 25. Each curtain 403 forms the upper edge of the central portions of one of slots 401c, and thus curtains 403 may be displaced from lower guard portion 401a by wings 203a to allow wings 203a to pass through such central slot portions (as shown in FIGS. 23 and 24). In FIG. 24, wings 203a displace curtains 403 radially outward with respect to the lower guard portion 401a (and thus radially outward with respect to the lower slot edges defined by portion 401a). Alternatively, curtains 403 could be shaped so that wings 203a will displace curtains 403 radially inward with respect to the lower guard portion 401a.

In another variation on the embodiment of FIGS. 23-25, the entire upper edge of each slot 401c (not just the central portion of such edge) is shaped so as to form one of curtains 403. In this case, the slots are sealed by pressing the upper slot edges (curtains 403) into a locked configuration against lower guard portion 401a (which defines the lower slot edges). The upper and lower slot edges in this embodiment would preferably have the same shapes as do the lips of conventional press-sealable plastic sandwich bags. Wings 203a would temporarily break apart (unseal) the slots as they translate through the slots during a transition from hub 203's extended position into hub 203's retracted position. After hub 203 and wings 203a have reached their fully retracted position, the slots would be resealed by pressing curtains 403 against lower guard portion 401a.

The invention may be manufactured using conventional winged needle assembly technology, and may be operated by medical personnel in a conventional manner with the simple additional step of holding the inventive guard fixed during extraction of the needle from a patient (such as by pressing the guard's anchor against a patient with one finger while simultaneously pressing gauze against the patient, in a conventional manner, with another digit of the same hand).

The foregoing is merely illustrative and explanatory of the invention. Various changes in the component sizes and shapes, and other details of the embodiments described herein may be within the scope of the appended claims.

What is claimed is:

1. A guard slidably enclosing a sliding assembly comprising a needle and a winged needle hub having a first wing and a second wing, said first and second wings each having generally planar portions joined to said needle hub and extending outwardly therefrom, said planar portions having a major and a minor dimension, the major dimension being located parallel with the needle length, said guard comprising:

a hollow member having a first, distal end and a second, proximal end separated along a longitudinal axis, and a side wall defining a first slot and a second slot, wherein the first slot slidably receives the first wing planar portion and a second slot slidably receives the second wing planar portion, said first and second wings projecting through said first and second slots, said wings being exposed to the exterior of the hollow member along essentially the entire slot length to permit manual grasping of the wings; and means for locking the sliding assembly in a retracted position in which the needle is enclosed by the hollow member after the sliding assembly has been translated along the longitudinal axis into the hollow member.

2. The guard of claim 1 which comprises an anchor member attached adjacent the first end of said hollow member and extending forwardly therefrom alongside of but spaced from said needle.

3. The guard of claim 2 in which said anchor member is substantially flexible, whereby it may be pressed against the skin of the patient when the needle is penetrating said skin.

4. The guard of claim 3 in which said hollow member comprises a first half-cylindrical portion and a second half-cylindrical portion attached together in hinged relation to permit assembly into a hollow member of generally cylindrical shape.

5. The guard of claim 4 in which said first and second wings are each flexible and substantially entirely planar in shape.

6. The guard of claim 1 in which said first and second wings are each flexible and substantially entirely planar in shape.

7. The guard of claim 1 in which said hollow member comprises a first half-cylindrical portion and a second half-cylindrical portion attached together in hinged relation to permit assembly into a hollow member of generally cylindrical shape.

* * * * *

UNITED STATES PATENT AND TRADEMARK OFFICE
CERTIFICATE OF CORRECTION

PATENT NO. : 5,266,072
DATED : November 30, 1993
INVENTOR(S) : David S. Utterberg and Neil J. Sheehan It is certified that error appears in the above-identified patent and that said Letters Patent is hereby corrected as shown below:

In the claims:

Claim 1, line 18, after "slot length";

insert -- and at least when the needle is fully extended from the hollow member --.

Signed and Sealed this

Second Day of November, 1999

*Attest:*

Q. TODD DICKINSON

*Attesting Officer*     Acting Commissioner of Patents and Trademarks